(12) United States Patent
Darde et al.

(10) Patent No.: US 9,206,041 B2
(45) Date of Patent: Dec. 8, 2015

(54) METHOD AND INSTALLATION FOR THE COMBINED PRODUCTION OF AMMONIA SYNTHESIS GAS AND CARBON DIOXIDE

(71) Applicant: L'Air Liquide, Société Anonyme pour l'Etude et l'Exploitation des Procédés Georges Claude, Paris (FR)

(72) Inventors: Arthur Darde, Paris (FR); Richard Dubettier-Grenier, La Varenne Saint Hilaire (FR)

(73) Assignee: L'Air Liquide, Société Anonyme pour l'Etude et l'Exploitation des Procédés George Claude, Paris (FR)

( * ) Notice: Subject to any disclaimer, the term of this patent is extended or adjusted under 35 U.S.C. 154(b) by 0 days.

(21) Appl. No.: 14/408,685

(22) PCT Filed: Jun. 6, 2013

(86) PCT No.: PCT/FR2013/051285
§ 371 (c)(1),
(2) Date: Dec. 17, 2014

(87) PCT Pub. No.: WO2014/001672
PCT Pub. Date: Jan. 3, 2014

(65) Prior Publication Data
US 2015/0191351 A1 Jul. 9, 2015

(30) Foreign Application Priority Data
Jun. 25, 2012 (FR) ........................... 12 56003

(51) Int. Cl.
C01B 3/38 (2006.01)
C01B 3/02 (2006.01)
(Continued)

(52) U.S. Cl.
CPC ................. *C01B 3/025* (2013.01); *B01J 19/24* (2013.01); *B01J 19/245* (2013.01); *C01B 3/34* (2013.01);
(Continued)

(58) Field of Classification Search
USPC ........................................................ 252/374
See application file for complete search history.

(56) References Cited

U.S. PATENT DOCUMENTS

2009/0298957 A1 12/2009 Gauthier et al.
2011/0094378 A1* 4/2011 Mitariten ................. 95/50
(Continued)

FOREIGN PATENT DOCUMENTS

CA 1268428 A1 5/1990
EP 0341879 A1 11/1989
(Continued)

OTHER PUBLICATIONS

International Search Report and Written Opinion for corresponding PCT/FR2013/051285, Jul. 22, 2013.

*Primary Examiner* — Melvin C Mayes
*Assistant Examiner* — Kenneth Vaden
(74) *Attorney, Agent, or Firm* — Justin K. Murray

(57) ABSTRACT

In a method for the combined production of ammonia synthesis gas and carbon dioxide from a mixture of hydrocarbons, the cooled mixture from a reverse conversion is separated in an adsorption unit by pressure modulation (or PSA) producing a hydrogen-enriched flow having a purity at least equal to 98% and a residual gas, the residual gas is processed to produce carbon dioxide and a gas containing nitrogen and methane and at least a portion of the hydrogen-enriched flow and at least a portion of the gas containing nitrogen and methane are mixed to form an ammonia synthesis gas.

13 Claims, 1 Drawing Sheet

(51) Int. Cl.
  *C01B 3/56* (2006.01)
  *C01C 1/04* (2006.01)
  *C07C 273/10* (2006.01)
  *B01J 19/24* (2006.01)
  *C01B 3/34* (2006.01)
  *C01B 31/20* (2006.01)

(52) U.S. Cl.
  CPC . *C01B 3/56* (2013.01); *C01B 31/20* (2013.01); *C01C 1/04* (2013.01); *C01C 1/0405* (2013.01); *C01C 1/0488* (2013.01); *C07C 273/10* (2013.01); *B01J 2219/24* (2013.01); *C01B 2203/0205* (2013.01); *C01B 2203/0283* (2013.01); *C01B 2203/042* (2013.01); *C01B 2203/043* (2013.01); *C01B 2203/048* (2013.01); *C01B 2203/0465* (2013.01); *C01B 2203/0475* (2013.01); *C01B 2203/0495* (2013.01); *C01B 2203/068* (2013.01); *C01B 2203/0872* (2013.01); *C01B 2203/1235* (2013.01); *C01B 2203/147* (2013.01); *C01B 2203/148* (2013.01); *C01B 2210/0014* (2013.01)

(56) References Cited

U.S. PATENT DOCUMENTS

2012/0011856 A1* 1/2012 Wright et al. .................. 60/780
2013/0017146 A1   1/2013 Darde et al.

FOREIGN PATENT DOCUMENTS

| EP | 2404869 A1 | 1/2012 |
| FR | 2958280 A1 | 10/2011 |
| FR | 2961802 A1 | 12/2011 |
| WO | 2006054008 A1 | 5/2006 |
| WO | 2010135185 A1 | 11/2010 |
| WO | 2011022591 A1 | 2/2011 |
| WO | 2012064938 A1 | 5/2012 |

\* cited by examiner

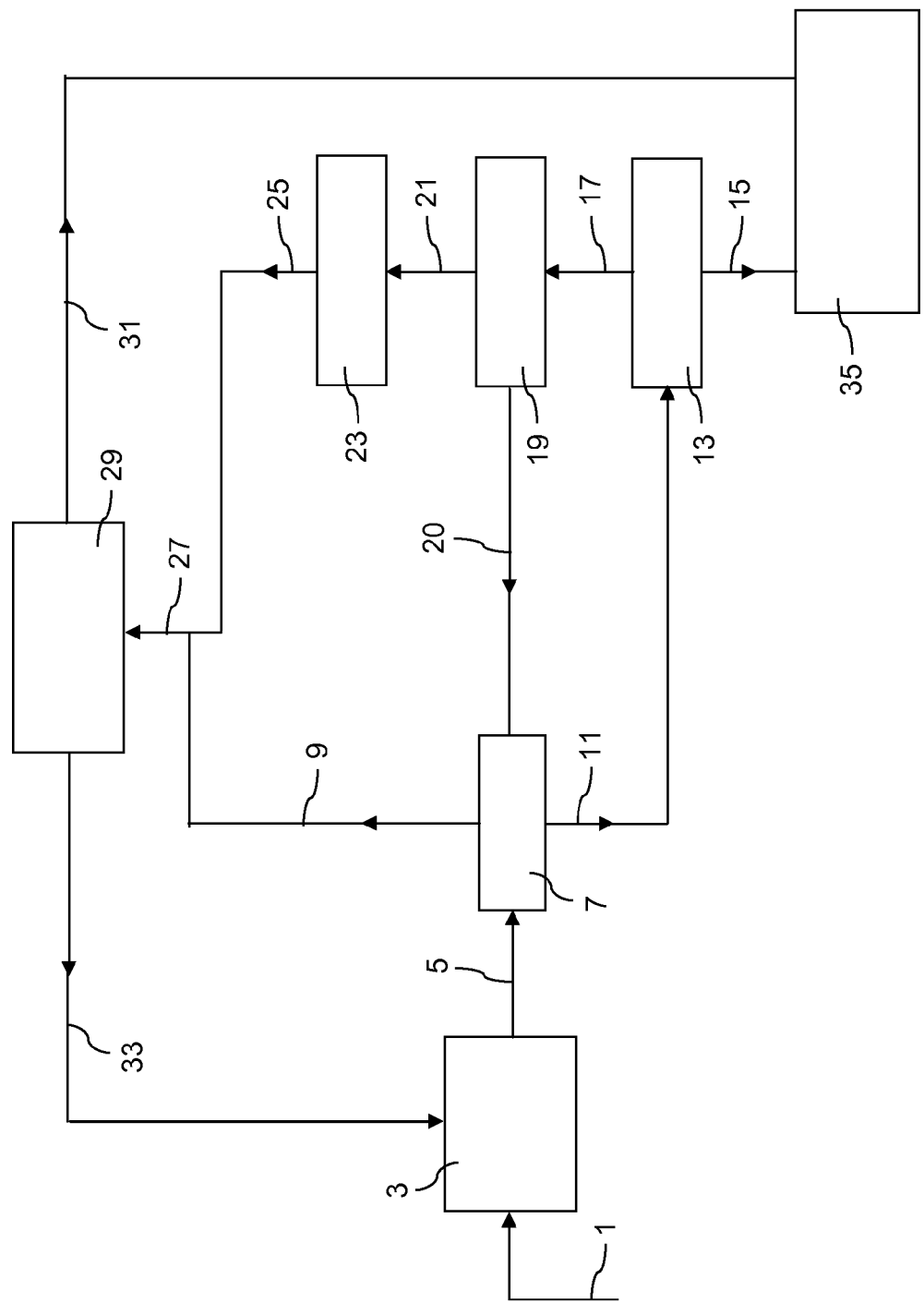

METHOD AND INSTALLATION FOR THE COMBINED PRODUCTION OF AMMONIA SYNTHESIS GAS AND CARBON DIOXIDE

CROSS REFERENCE TO RELATED APPLICATIONS

This application is a §371 of International PCT Application PCT/FR2013/051285, filed Jun. 6, 2013, which claims the benefit of FR1256003, filed Jun. 25, 2012, both of which are herein incorporated by reference in their entireties.

TECHNICAL FIELD OF THE INVENTION

The present invention relates to a method and installation for the combined production of ammonia synthesis gas and carbon dioxide from a hydrocarbon source. More specifically, the present invention relates to a method for the combined production of ammonia synthesis gas and carbon dioxide from a synthesis gas produced by reforming hydrocarbons, and natural gas in particular.

The invention also relates to a method and an installation for integrated production of ammonia and carbon dioxide and a method and an installation for urea production.

BACKGROUND

All the purity percentages are molar percentages.

From WO-A-06/054008 it is known how to produce carbon dioxide from a PSA tail by treating a gas from a reverse conversion.

The main steps in the ammonia synthesis are:
1. steam reforming natural gas (or another carbon-containing fuel).
2. second reforming/partial oxidation in air, to add nitrogen for the ammonia synthesis reaction.
3. reacting CO into $CO_2$ and $H_2$ on a catalyst.
4. extracting $CO_2$ by washing with a solvent (aMDEA®, Benfield method, etc.).
5. methanating traces of CO and $CO_2$ into $CH_4$ and $H_2O$ on a catalyst using a high hydrogen excess (CO and $CO_2$ being poisons for the catalyst).
6. ammonia synthesis with two possible variants:
    a. dry+wash with nitrogen to adjust the $H_2/N_2$ ratio to 3 and extract surplus $CH_4$, argon and $N_2+NH_3$ synthesis loop via catalytic reactors,
    b. or: $NH_3$ synthesis loop via catalytic reactors+treat the purge evacuating $CH_4$, argon and excess $N_2$ on a PSA to recover the $H_2$.

When there is a desire to further use the $CO_2$ extracted in step 4 (for example to make oil extraction easier or to produce a chemical such as urea, etc.) or if there is a desire to sequester it to reduce greenhouse gas emissions, a compression and drying step for the $CO_2$ extracted in step 4 must be added.

The invention proposed aims to significantly reduce the cost of $NH_3$ production when the $CO_2$ must be compressed to be further used as described above.

Therefore there is a need for an economically viable method for producing ammonia synthesis gas and carbon dioxide.

SUMMARY OF THE INVENTION

According to an object of the invention, a method for the combined production of ammonia synthesis gas and carbon dioxide from a hydrocarbon mixture is provided, including at least:
one purification step for the cooled mixture from the/a reverse conversion in an adsorption unit by pressure modulation (or PSA) allowing a hydrogen-enriched flow to be produced at a purity at least equal to 98% and a tail gas called a "PSA tail" containing carbon dioxide, nitrogen, methane and carbon monoxide, at a pressure of the order of 1 to 3 bar abs,
and a treatment step for said PSA tail to produce a carbon dioxide-enriched fluid, including at least:
one compression step for the PSA tail up to a pressure greater than the reforming pressure and such that the partial pressure of the $CO_2$ contained is comprised between about 25 and 35 bar;
a drying step for the compressed PSA tail by eliminating the water contained to produce a dry gas;
one or more successive condensation/separation steps, such that
each of the steps comprises in itself:
a step of condensing all or part of the $CO_2$ contained in the gas coming from the previous step, followed by
a step of separating the $CO_2$-rich condensate from the separation with the gas phase containing the non-condensable compounds, optionally by distillation
and,
the step or steps are implemented at temperatures comprised between room temperature and −56° C.,
a $CO_2$-depletion step of a gas phase from at least one separation step, for example a permeation separation, to produce a $CO_2$-depleted flow and a $CO_2$-enriched flow
a methanation step for the $CO_2$-depleted flow to produce a gas containing nitrogen and methane, and
a step of mixing at least a portion of the hydrogen-enriched flow and at least a portion of the gas containing nitrogen and methane to form an ammonia synthesis gas.

According to other optional features:
the $CO_2$-depleted flow is sent for methanation at a pressure of at least 35 bars,
the $CO_2$-enriched flow coming from the $CO_2$-depletion step is sent to the adsorption unit by pressure modulation,
the method comprises a steam reverse conversion step for synthesis gas to oxidize the major portion of the carbon monoxide that it contains into carbon dioxide, with corresponding hydrogen production and
the method comprises a reforming step for the hydrocarbon mixture to produce a synthesis gas containing at least carbon dioxide, hydrogen, carbon monoxide, methane, and steam;

According to a further object of the invention, a method is provided for ammonia and carbon dioxide production as described above in which the ammonia synthesis gas is treated in a treatment unit to produce an ammonia flow and a gas containing methane and nitrogen.

Optionally:
the gas containing methane and nitrogen is sent back to the reforming step,
all the nitrogen sent to the treatment unit is contained in at least a portion of the hydrogen-enriched flow and at least a portion of the gas containing the nitrogen and the methane mixed to form an ammonia synthesis gas and
the ammonia is reacted with the carbon dioxide to produce urea.

According to a further object of the invention, an apparatus is provided for the combined production of ammonia synthesis gas and carbon dioxide from a hydrocarbon mixture, including at least:
one purification unit for the cooled mixture from a reverse conversion in an adsorption unit by pressure modulation (or PSA) allowing a hydrogen-enriched flow to be produced at a purity at least equal to 98% and a tail gas called a "PSA tail" containing carbon dioxide, nitrogen, methane and carbon monoxide, at a pressure of the order of 1 to 3 bar abs, and a treatment unit for said PSA tail to produce a carbon dioxide-enriched fluid, including at least:
  a unit for compressing the PSA tail up to a pressure greater than the reforming pressure and such that the partial pressure of the $CO_2$ contained is comprised between about 25 and 35 bar;
  a unit for drying the compressed PSA tail by eliminating the water contained to produce a dry gas;
  a unit where several successive condensation/separation steps occur, such that
  each of the steps comprises in itself:
  a step of condensing all or part of the $CO_2$ contained in the gas coming from the previous step, followed by
  a step of separating the $CO_2$-rich condensate from the separation with the gas phase containing the non-condensable compounds, optionally by distillation
  and,
  the step or steps are implemented at temperatures comprised between room temperature and −56° C.,
  a $CO_2$-depletion step for a gas phase from at least one separation step, for example by permeation, to produce a $CO_2$-depleted flow and a $CO_2$-enriched flow,
  a methanation unit for the $CO_2$-depleted flow to produce a gas containing nitrogen and methane and
  means for mixing at least a portion of the hydrogen-enriched flow and at least a portion of the gas containing nitrogen and methane to form an ammonia synthesis gas.

The apparatus may comprise means for sending the $CO_2$-enriched flow coming from the $CO_2$-depletion step back to the adsorption unit by pressure modulation.

According to a further object of the invention, an apparatus is provided for ammonia and carbon dioxide production as described above comprising a treatment unit to treat the ammonia synthesis gas to produce an ammonia flow and a gas containing methane and nitrogen.

The apparatus may comprise means to send the gas containing methane and nitrogen back to the reforming step.

The apparatus may comprise a steam reverse conversion unit for synthesis gas to oxidize the major portion of the carbon monoxide that it contains into carbon dioxide, with corresponding hydrogen production.

The apparatus may comprise a reforming unit for the hydrocarbon mixture to produce a synthesis gas containing at least carbon dioxide, hydrogen, carbon monoxide, methane, and steam.

The apparatus may comprise a unit in which the ammonia is reacted with the carbon dioxide to produce urea.

The solution according to the invention consists in using non-condensable gases from a carbon dioxide production method by low-temperature separation to supply an ammonia synthesis production unit.

Without a decarbonation step, but with a reverse conversion step, the PSA residue contains a quantity of $CO_2$ of the order of 45% coming from reforming and the reverse conversion (the exact $CO_2$ content naturally being a function of the composition of the initial hydrocarbon mixture). Thus, starting from PSA tail gas, whose pressure is typically less than 2 bar, the method allows for having a total gas pressure due to compression comprised between 40 and 80 bar, corresponding to a $CO_2$ partial pressure comprised between 15 and 40 bar, compatible with cryogenic purification. These pressures will allow the fluids to be used in the remainder of the method without being obliged to conduct extra compressions.

The PSA tail is therefore purified by partial condensation and optionally by permeation to produce a $CO_2$-rich liquid flow. This liquid can, due to appropriate extra treatments, be used or sequestered on-site or nearby in gaseous form; it can be exported to be used or sequestered in gaseous or liquid form. It can in particular and in a particularly advantageous manner be used in the food industry, thanks to suitable purification.

If the $CO_2$ produced is not to be used on-site or nearby, and according to a first specific embodiment, all or part of the liquid is vaporized after decompression, with recovery of cold, to produce $CO_2$ in gaseous form under a pressure comprised between 10 and 35 bar. The cold recovered is advantageously used to cool fluids of the method as a complement to refrigeration apparatuses. The $CO_2$ could then be compressed to be transported by gas pipeline to a use and/or sequestration site.

According to another embodiment, but still if the $CO_2$ produced is not to be used on-site or nearby, all or part of the liquid could be transported in this form to a use and/or sequestration site.

The method is most particularly advantageous when it is implemented to optimize the production of ammonia synthesis gas and to produce carbon dioxide jointly.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

The FIGURE provides an embodiment of the invention.

DETAILED DESCRIPTION

The invention will now be described by referring to the drawings and examples below.

The drawings illustrate specific embodiments of the method of the invention.

It must be understood that the invention is not limited to these embodiments. The person of skill in the art will in particular be able to envisage combining the treatment and recycling techniques illustrated in these embodiments.

The FIGURE shows a functional diagram illustrating an embodiment of the invention to produce ammonia synthesis gas and carbon dioxide, respectively, for example carbon dioxide to be sequestered.

The feed supplying the method is made of a mixture of hydrocarbons—here natural gas (NG)—the flow 1 of hydrocarbons feeds an installation 3 comprising a desulfuration unit, a pre-reformer to produce a pre-reformed mixture, a mixture essentially constituted of methane, hydrogen, carbon monoxide, carbon dioxide and water, a reforming module supplied by the pre-reformed mixture that produces a synthesis gas containing essentially hydrogen, carbon monoxide, carbon dioxide, methane and steam and a reverse conversion module.

The synthesis gas is cooled and then the cooled gas is treated in this reverse conversion module, where the CO is converted into $H_2$ and $CO_2$. The gaseous mixture 5 exiting installation 3 is cooled and then treated in a hydrogen purification unit 7 such as an adsorption unit by pressure modulation or PSA, to produce a hydrogen-enriched gas flow 9 at a purity at least equal to 98% and a tail gas 11—called a PSA tail—containing carbon dioxide, methane, nitrogen, argon, hydrogen and carbon monoxide. This PSA tail 11 is available at a pressure of the order of 1 to 3 bar abs and it contains approximately all the $CO_2$ coproduced during the reforming and reverse conversion steps. Typically, in the case of FIG. 1 where the hydrocarbon mixture 1 supplying the method is natural gas, the average composition of the PSA tail 11 is similar to: $CO_2$: 45%-CO: 12%-$H_2$: 23%-$CH_4$: 17%-$H_2O$: 1%-$N_2$: 2%. Taking into account composition variations related to the PSA unit's cycle, the $CO_2$ content is comprised between 42 and 48%, the $H_2$ content varies between 20 and 26%, and the contents of the other constituents remain approximately constant.

The PSA tail 11 is then purified in a purification unit 13. The PSA tail 11 is first compressed in a compression module in the purification unit, to produce a compressed PSA tail. It is compressed at about 60 bar, which ensures a $CO_2$ partial pressure of the order of 27 bar. Next it is cleared of heavy impurities in an adsorption module in the purification unit, by a succession of adsorptions that can be regenerated, for example, to produce a purified compressed tail that is next dried in a drying module in a purification unit to produce a compressed tail, cleared of heavy impurities and dried.

This tail is then cooled to be separated by liquefaction in a separation module forming a portion of the purification unit, which produces a liquid 15 containing essentially liquid $CO_2$ and a gaseous mixture 17 containing a non-condensed $CO_2$ fraction and the lighter compounds that are called non-condensables.

The tail 11 is cooled by counter-current circulation of cold fluids from cryogenic purification and/or by heat exchange with an associated external refrigeration group. The liquid 15 contains essentially $CO_2$, however to produce pure $CO_2$, the liquid 15 results from a distillation with the goal of clearing light impurities carried along in the liquid phase. For this, the tail can be decompressed to 23 bar before supplying the distillation column.

The gas phase 17 produced from the separation contains the light impurities from the feed 1 and is at at least 40 bars abs; heated to room temperature in the heat exchangers, it constitutes the purge of non-condensables, available at a pressure of 58 bar. The composition of the purge is of of: $CO_2$: 21%-CO: 18%-$H_2$: 36%-$CH_4$: 24%-$N_2$: 1%.

The purge of non-condensables 17 is then treated in the adsorption or permeation module of a $CO_2$ depletion unit 19 to reduce its carbon dioxide content. A gas produced 21 has reduced carbon dioxide content. The other gas produced 20, which is $CO_2$-rich and hydrogen-rich, is sent to the PSA unit 7 to improve its yield, without being mixed upstream with the flow 5.

Indeed, the yield of the PSA unit 7 is very low because of the high $N_2$ content; one way to improve it is to introduce the gas 20 (optionally being a permeate), which is certainly richer in $H_2$ than the PSA supply, at the right moment in the cycle, to improve the PSA yield. The PSA unit differs from standard $H_2$ PSA that must stop CO/$CO_2$ and $N_2$. The unit 7 to stop the CO and the $CO_2$, but can let the nitrogen pass, which means the $H_2$ yield of the PSA unit 7 does not have to be penalized.

The gas 21 is next treated by methanation in a methanation unit 23 to transform the carbon dioxide and carbon monoxide remainders into methane, forming a gas 25.

The gas 25 is mixed with pure hydrogen 9 to form an ammonia synthesis gas 27. The ammonia synthesis gas 27 is sent to an ammonia synthesis unit 29 to produce ammonia 31.

The ammonia synthesis unit also produces a gas 33 containing methane, nitrogen, argon, and hydrogen, which is sent back to unit 3.

Optionally ammonia 31 and carbon dioxide 15 may supply a urea production unit 35.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a non-exclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary a range is expressed, it is to be understood that another embodiment is from the one.

Optional or optionally means that the subsequently described event or circumstances may or may not occur. The description includes instances where the event or circumstance occurs and instances where it does not occur.

Ranges may be expressed herein as from about one particular value, and/or to about another particular value. When such particular value and/or to the other particular value, along with all combinations within said range.

All references identified herein are each hereby incorporated by reference into this application in their entireties, as well as for the specific information for which each is cited.

The invention claimed is:

1. A method for the combined production of ammonia synthesis gas and carbon dioxide from a hydrocarbon mixture, the method comprising the steps of:
 reforming the hydrocarbon mixture in a reformer operating at a reforming pressure to produce a hot mixture consisting essentially of hydrogen, carbon monoxide, carbon dioxide, methane and steam and then cooling the hot mixture to produce a cooled mixture;
 obtaining the cooled mixture from a reverse conversion and purifying the cooled mixture in an adsorption unit by pressure swing adsorption (PSA) allowing a hydrogen-enriched flow to be produced at a purity at least equal to 98% and a tail gas called a PSA tail, the PSA tail comprising carbon dioxide, nitrogen, methane and carbon monoxide, at a pressure of the order of 1 to 3 bar abs; and
 treating said PSA tail to produce a carbon dioxide-enriched fluid,
wherein the step of treating said PSA tail further comprises the steps of:
 compressing the PSA tail up to a pressure greater than the reforming pressure such that the partial pressure of the $CO_2$ is between about 25 and 35 bar;
 drying the compressed PSA tail by removing water to produce a dry gas, the dry gas having $CO_2$ and non-condensable compounds;
 one or more successive condensation/separation steps, such that
 each of the successive condensation/separation steps comprises in itself:
  condensing all or part of the $CO_2$ contained in the gas coming from the previous step to form a $CO_2$-rich condensate, followed by
  separating the $CO_2$-rich condensate from a gas phase containing the non-condensable compounds, and,
each of the successive condensation/separation steps step or steps are implemented at temperatures comprised between room temperature and −56° C.;
a $CO_2$-depletion step of the gas phase containing the non-condensable compounds from at least one separation step to produce a $CO_2$-depleted flow and a $CO_2$-enriched flow;
a methanation step of the $CO_2$-depleted flow to produce a gas containing nitrogen and methane; and
mixing at least a portion of the hydrogen-enriched flow and at least a portion of the gas containing nitrogen and methane to form an ammonia synthesis gas.

2. The method as claimed in claim 1, wherein the $CO_2$-depleted flow is sent to the methanation at a pressure of at least 35 bars.

3. The method as claimed in claim 1, wherein the $CO_2$-enriched flow coming from the $CO_2$-depletion step is sent to the adsorption unit by pressure modulation.

4. The method as claimed in claim 1 further comprising a steam reverse conversion step for synthesis gas to oxidize the major part of the carbon monoxide that it contains into carbon dioxide, with corresponding hydrogen production.

5. The method as claimed in claim 1, wherein all the nitrogen sent to the ammonia synthesis unit comes from the methanation of the $CO_2$-depleted flow or from the hydrogen-enriched flow.

6. The method as claimed in claim 1, wherein the ammonia synthesis gas is treated in a treatment unit to produce an ammonia flow and a gas containing methane and nitrogen.

7. The method as claimed in claim 6, wherein the gas containing methane and nitrogen is sent back to the reforming step.

8. The method as claimed in claim 6, wherein ammonia is reacted with carbon dioxide to produce urea.

9. An apparatus for the combined production of ammonia synthesis gas and carbon dioxide from a hydrocarbon mixture, including at least:
a purification unit configured to receive a cooled mixture from a reverse conversion, the purification unit comprising an adsorption unit configured to treat the cooled mixture by pressure modulation thereby producing a hydrogen-enriched flow having a purity at least equal to 98% and a tail gas called a "PSA tail" containing carbon dioxide, nitrogen, methane and carbon monoxide, at a pressure of the order of 1 to 3 bar abs, wherein the adsorption unit comprises a cooled mixture inlet, a hydrogen outlet, and a tail gas outlet; and
a tail gas treatment unit configured to receive said PSA tail from the purification unit, wherein the tail gas treatment unit is configured to produce a carbon dioxide-enriched fluid, wherein the tail gas treatment unit further comprises:
a compression unit for compressing the PSA tail up to a pressure greater than the reforming pressure and such that the partial pressure of the $CO_2$ contained is comprised between about 25 and 35 bar;
a drying unit for drying the compressed PSA tail by eliminating the water contained to produce a dry gas, the dry gas having $CO_2$ and non-condensable compounds;
a condensation/separation unit where one or more successive condensation/separation steps take place, such that
each of the steps comprises in itself:
a step of condensing all or part of the $CO_2$ contained in the gas coming from the previous step, followed by
a step of separating the $CO_2$-rich condensate from a gas phase containing the non-condensable compounds,
and,
the step or steps are implemented at temperatures comprised between room temperature and −56° C.;
a $CO_2$-depletion unit configured to receive a gas phase from at least one separation step and produce a $CO_2$-depleted flow and a $CO_2$-enriched flow;
a methanation unit configured to receive the $CO_2$-depleted flow and produce a gas containing nitrogen and methane; and
an ammonia synthesis gas conduit in fluid communication with the methanation unit and the hydrogen outlet of the adsorption unit, such that the ammonia synthesis gas conduit is configured to receive at least a portion of the hydrogen-enriched flow and at least a portion of the gas containing nitrogen and methane to form an ammonia synthesis gas.

10. The apparatus as claimed in claim 9 further comprising a ammonia synthesis gas treatment unit in fluid communication with the ammonia synthesis gas conduit, the ammonia synthesis gas treatment unit configured to treat ammonia synthesis gas to produce an ammonia flow and a gas containing methane and nitrogen.

11. The apparatus as claimed in claim 10 further comprising a urea production unit in fluid communications with the ammonia synthesis gas treatment unit and the tail gas treatment unit, such that the urea production unit is configured to receive the ammonia flow from the ammonia synthesis gas treatment unit and the carbon dioxide flow from the tail gas treatment unit.

12. The apparatus as claimed in claim 9 further comprising a steam reverse conversion unit for all or part of a synthesis gas to oxidize the major portion of the carbon monoxide that the synthesis gas contains into carbon dioxide, with corresponding hydrogen production.

13. The apparatus as claimed in claim 12 further comprising a reforming unit for the hydrocarbon mixture to produce a synthesis gas containing at least carbon dioxide, hydrogen, carbon monoxide, methane, and steam.

* * * * *